United States Patent [19]
Lambert et al.

[11] Patent Number: 5,462,048
[45] Date of Patent: Oct. 31, 1995

[54] HEAT AND MOISTURE EXCHANGER

[75] Inventors: Hans Lambert, Stockholm; Jan Grebius, Sollentuna, both of Sweden

[73] Assignee: Gibeck Respiration AB, Upplands Vaesby, Sweden

[21] Appl. No.: 305,914

[22] Filed: Sep. 15, 1994

[30] Foreign Application Priority Data

Sep. 17, 1993 [SE] Sweden .................................. 9303044

[51] Int. Cl.$^6$ ........................... A61M 16/00; A62B 18/08
[52] U.S. Cl. .................. 128/201.13; 128/203.16; 128/203.27
[58] Field of Search ...................... 128/201.13, 203.16, 128/203.17, 203.26, 203.27, 204.17, 207.14

[56] References Cited

U.S. PATENT DOCUMENTS

| | | | |
|---|---|---|---|
| 3,912,795 | 10/1975 | Jackson | 128/207.14 |
| 4,090,513 | 5/1978 | Togawa | 128/207.14 |
| 4,971,054 | 11/1990 | Andersson et al. | 128/207.14 |
| 5,022,394 | 6/1991 | Chmielinski | 128/207.14 |
| 5,109,471 | 4/1992 | Lang | 128/207.14 |
| 5,255,674 | 10/1993 | Oftedal et al. | 128/203.16 |

FOREIGN PATENT DOCUMENTS

| | | | |
|---|---|---|---|
| 9119527 | 12/1991 | European Pat. Off. | 128/203.26 |
| 3928530 | 6/1990 | Germany | 128/203.26 |

*Primary Examiner*—Edgar S. Burr
*Assistant Examiner*—V. Srivastava
*Attorney, Agent, or Firm*—Oblon, Spivak, McClelland, Maier & Neustadt

[57] ABSTRACT

A heat and moisture exchanger, which is intended to be connected to a patient to humidify and warm the air inhaled by him, comprises a heat and moisture exchanger unit which includes a plurality of axially oriented layers and a warming device disposed adjacent thereto to increase the heat supply to the air inhaled. The exchanger further includes a humidifying device to increase the humidity of the air inhaled. The humidifying device includes a diffusion rod bearing on one end surface of the heat and moisture exchanger unit, the length of the diffusion rod being substantially equal to the radial extension of the heat and moisture exchanger.

12 Claims, 1 Drawing Sheet

HEAT AND MOISTURE EXCHANGER

TECHNICAL FIELD

The present invention relates to a heat and moisture exchanger, which is intended to be connected to a patient to humidify and warm the air inhaled. On the side farthest away from the patient, the heat and moisture exchanger is usually connected to a respirator.

PRIOR ART

Heat and moisture exchangers of the above stated kind are previously known. A heat and moisture exchanger of this kind is disclosed in U.S. Pat. No. 5,109,471. The heat and moisture exchanger comprises two passive heat and moisture exchanger elements and an intermediate warming and humidifying device. Humidification is carried out in that water, brought into ducts in the device, wets a perforated paperboard disc covering the end surface of one of the heat and moisture exchanger elements. Heating of the water in the heat and moisture exchanger is carried out by means of resistors and thereby heated heat distribution means, including a perforated disc, which are disposed between the two passive heat and moisture exchanger elements.

The humidifying device in the known apparatus causes the air flowing through the heat and moisture exchanger to be exposed to a considerable flow resistance, slowing down the speed of the air and reducing the through flow of inhalation and exhalation air. This is mainly due to the perforated discs covering large portions of the flow area.

The warming device in the known apparatus is designed in such a way that the air flowing through it is warmed only partially and, in addition, unevenly. The warming device being disposed in an area between the two passive heat and moisture exchangers implies a large axial extension of the heat and moisture exchanger.

Another apparatus known from U.S. Pat. No. 4,601,287 comprises a mask protecting a user from inhaling cold air. It includes a casing with heating coils embedded in a thread material. This apparatus is not a true heat and moisture exchanger. It has no humidifying device and provides a rather hot and dry inhalation air. Further, warming of the inhalation air is uneven and incomplete.

From DE-A1 4 126 028 there is known a heat and moisture exchanger including a heat and moisture exchanger element, into which a plurality of conduits project, which conduits supply water to the element, thus humidifying it. The apparatus also includes a warming device comprising an annular heating element spaced apart from the heat and moisture exchanger element both radially and axially. The major disadvantage of this apparatus is that both warming and humidification of the respiratory air is inefficient mainly due to the large distance between the warming device and the heat and moisture exchanger element and to the fact that water is supplied to only a few discrete areas in the heat and moisture exchanger element. In addition, the large distance between the warming device and the heat and moisture exchanger element causes the axial and radial extension of the apparatus to be unnecessarily large.

From WO91/19527 there is known a heat and moisture exchanger including a heat and moisture exchanger element in the form of a disc and a resistance spaced apart from the disc for warming respiratory air. The apparatus further includes a duct which opens at the surface of the resistance, supplying water thereto. The major disadvantages of this apparatus are that humidification is inefficient owing to water being supplied to the resistance and not to the heat and moisture exchanger element, and that warming is incomplete where the resistance is formed as a rod, or the air flow is impaired where the resistance is formed as a grid.

SUMMARY OF THE INVENTION

It is an object of the present invention to eliminate at least partly the disadvantages of previously known heat and moisture exchangers and to provide a heat and moisture exchanger which provides efficient humidification and warming of the air inhaled, as well as a low flow resistance of the respiratory air and small dimensions of the apparatus.

This object is achieved in that the apparatus according to the invention has been given the features stated in the characterizing portions of the claims.

PREFERRED EMBODIMENT

Figure 1:
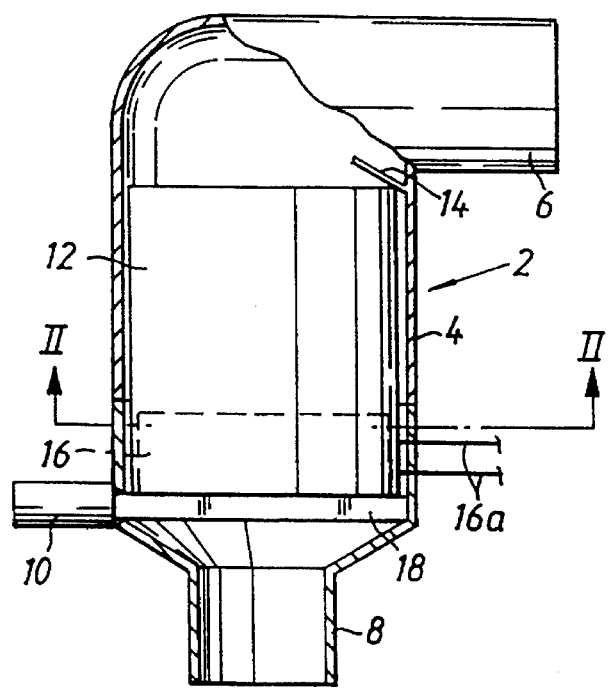
FIG. 1 is a side view of an apparatus according to the invention, partly in section.
Figure 4:
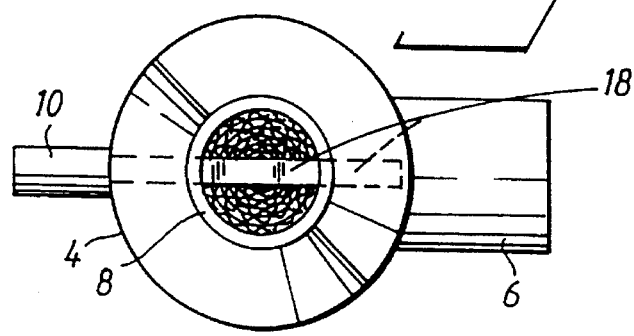
FIG. 4 is a view of the apparatus in FIG. 1 seen from below.
Figure 2:
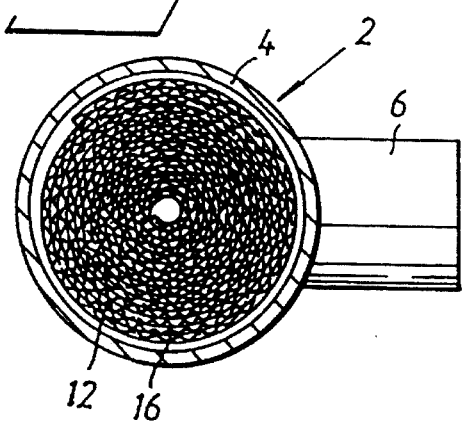
FIG. 2 is a sectional view along the line II—II in FIG. 1.
Figure 3:
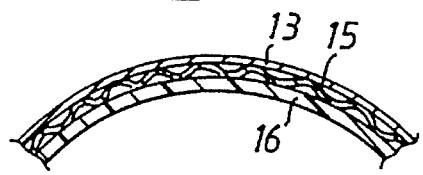
FIG. 3 is an enlarged partial view of FIG. 2.

The apparatus according to FIGS. 1–3 comprises a casing 2 consisting preferably of a transparent, rigid plastic material and having a circular cylindrical intermediate portion 4, a tubular inlet portion 6 oriented transversely thereto and whose circular cross section is smaller than that of the intermediate portion 4, and a tubular outlet portion 8 which is concentrical with the intermediate portion 4 and whose circular cross section is smaller than that of the intermediate portion 4 but essentially equal to the cross section of the inlet portion 6. If desired, the inlet portion 6 may instead be concentric with the portions 4 and 8. A tubular inlet connection piece 10, in the form of a so called Luer mount, is attached to the lower part of the intermediate portion 4 and communicates with the inside of the casing 2 via an aperture in the side wall of the intermediate portion 4.

The casing 2 is suitably formed in two separate parts, i.e. one part comprising the intermediate portion 4 and the inlet portion 6 and the other part comprising the outlet portion 8, which two production part have been interconnected after insertion of the necessary components therein.

The casing 2 contains a circular cylindrical heat and moisture exchanger unit 12. The envelope surface of the unit 12 bears on the inner wall of the intermediate portion 4 or is located at a short distance therefrom. A radially outer area of the upper end surface of the unit 12 bears on an inwardly oriented part 14 of the inlet portion 6 to prevent the unit from being displaced within the casing 2. The unit 12 is made of a material with good heat and moisture exchanging properties and is formed as a band which is wound into a helical shape so as to form a plurality of substantially concentric layers which are substantially parallel to the direction of flow of the respiratory air. A suitable unit of this kind could be, for instance, the unit included in a heat and moisture exchanger marketed by Gibeck Respiration AB under the trademark Humid-Vent 2S, which unit comprises a band helically wound into a cylinder and consisting of a paper layer 13 with a smooth surface and a layer 15 of corrugated paper attached thereto, which layers are optionally treated with a germicide or other agent. The band may have a length of, for instance, 1000 mm and a thickness of, for instance, 1 mm.

A warming device 16 is integrated in the unit 12 in that it is inserted between plural layers of the same. The device 16 consists of a band which includes one or more resistor elements and is wound into a helical shape along with the unit 12, such that every other layer is formed by the band 16 and every other layer is formed by the band of which the unit 12 is made. The band 16 has a small thickness, for instance around 0,2 mm, and a width of, for instance, around 10 mm which is less than the height of the unit 12. The height of the unit 12 may be around 40 mm and its diameter around 37 mm. The length of the band may be around 800 mm. The band 16 is disposed in the lower part of the unit 12, one longitudinal edge thereof being approximately aligned with the lower end surface of the unit. The band 16 is suitably made of electrically inductive plastic and is formed as a PTC (positive temperature coefficient) element, i.e. is self-regulating, and emits heat of around 45° C. Instead of a band one or more wires may be used.

One end of the band 16, the outer one in FIG. 1, is provided with two connecting wires 16a projecting through apertures in the side wall of the intermediate portion 4 for connection to an electric power supply (not shown).

A humidifying device 18 is disposed within the casing 2 in contact with the lower end surface of the unit 12. The device 18 consists of a diffusion bar or rod of cylindrical or rectangular cross section, whose dimensions may be 3×3×37 mm and which is made of a hydrophilic material, such as porous plastic of polyethylene or polypropene, or a fiber material, such as polyester or cellulose. The rod 18 is approximately the same length as the radial extension, i.e. diameter, of the unit 12 and is pressed into place between the unit and the conical upper part of the outlet portion 8. One end of the rod 18 is located just opposite the aperture in the side wall of the intermediate portion 4 communicating with the connection piece 10 or is inserted therein. The rod 18 extends across the diameter of the unit 12, taking up a small part of the flow area of the intermediate portion 4. The connection piece 10 is intended to be connected to a water supply from which water is supplied to the rod 18 either by gravity or by a pump. In this way, the rod is wetted without giving off water in the form of drops. By the rod 18 being in contact with substantially all of the layers of the unit 12, the water diffuses into the material thereof in two places for each layer. The water absorbent material is hereby humidified in such a way that substantially all of the lower part of the unit 12 is wetted.

The apparatus according to the invention is intended to be connected to a system for improving the respiratory conditions of a patient. Thus, for example, the inlet portion 6 is connected to a respirator (not shown) and the outlet portion 8 to the patient. During the inhalation phase of the patient the inhalation air will flow from the respirator through the inlet portion 6 and via the intermediate portion 4 out through the outlet portion 8 to the patient. The air is hereby warmed and humidified by the unit 12. The air is warmed in that during the preceding exhalation phase the unit 12 has been warmed up by the air exhaled and in that the lower part of the unit 16 is warmed by the device 16. The heat emitted by the device 16 is distributed to the adjacent layers in the unit and the interspaces between these substantially over the entire cross sectional area thereof, implying that the air inhaled will be substantially evenly heated. The air is humidified by the unit having been humidified by the air exhaled during the preceding exhalation phase and by at least the lower part of the unit being humidified by the device 18. The water supplied by the device 18 will spread to all layers in the unit substantially over the entire cross sectional area thereof, implying that the inhalation air will be substantially uniformly humidified.

During the exhalation phase of the patient the air exhaled will flow in the opposite direction through the apparatus, the upper part of the unit 12 cooling and dehumidifying the air before it enters, for instance, a respirator.

In the foregoing, one embodiment of the present invention has been described and shown in the drawings but other embodiments as well as modifications of said embodiment are possible without departing from the principle of the invention. Instead of using helically wound layers in the unit 12, it is thus possible to use layers shaped as a concertina or consisting of separate parallel layers, in which case, however, the design of the warming device 16 must be adapted accordingly.

The invention is only limited by what is stated in the claims.

We claim:

1. A heat and moisture exchanger adapted to be connected to a patient to humidify and warm air which is inhaled by the patient, the heat and moisture exchanger comprising:

a heat and moisture exchanger unit which comprises a plurality of layers oriented substantially parallel to a direction of air flow; and a warming device disposed adjacent to the heat and moisture exchanger unit to increase a heat supply to the inhaled air, said warming device being interposed between at least two of the layers of the heat and moisture exchanger unit.

2. A heat and moisture exchanger according to claim 1, wherein the warming device is band-shaped.

3. A heat and moisture exchanger according to claim 1, wherein the heat and moisture exchanger unit comprise at least one band of a heat and moisture exchanging material wound into a helical shape, so as to form a cylinder, the warming device being interposed between at least two of the layers of the band.

4. A heat and moisture exchanger according to claim 3, wherein the warming device formed of a band is wound together with the band so as to form a helix.

5. A heat and moisture exchanger according to claim 4, wherein a longitudinal axis of the cylinder is longer than an axial width of the band and the band is attached at an end part of the cylinder which is nearest to the patient.

6. A heat and moisture exchanger according to claim 1, wherein the warming device comprises a positive temperature coefficient element.

7. A heat and moisture exchanger according to claim 1, wherein the warming device is wired-shaped.

8. A heat and moisture exchanger according to claim 1 including:

a humidifying device disposed adjacent to the heat and moisture exchanger unit to increase the humidity of inhaled air, the humidifying device comprising a diffusion rod bearing on one end surface of the heat and moisture exchanger unit, a length of the diffusion rod being substantially equal to an extension of the heat and moisture exchanger unit in a direction perpendicular to a direction of air flow through the heat and moisture exchanger.

9. A heat and moisture exchanger according to claim 8, wherein the warming device and the diffusion rod are disposed adjacent to each other at an end of the heat and moisture exchanger unit located nearest to the patient.

10. A heat and moisture exchanger according to claim 8, further comprising a water inlet connection piece disposed on the heat and moisture exchanger, the rod being connected to the water inlet connection piece.

11. A heat and moisture exchanger which is to be connected to a patient to humidify and warm air inhaled by the patient, the heat and moisture exchanger comprising:

a heat and moisture exchanger unit which comprises a plurality of layers oriented substantially parallel to a direction of air flow; and a warming device for increasing a heat supply to the inhaled air, said warming device being integrated in a lower portion of the heat and moisture exchanger unit such that the warming device is interposed between at least two of the layers of the heat and moisture exchanger unit.

12. A heat and moisture exchanger unit according to claim 11, wherein said warming device comprises means for connecting the warming device to an electrical power supply.

* * * * *